United States Patent [19]

Kloek

[11] 4,265,657
[45] May 5, 1981

[54] HERBICIDAL COMPOSITIONS CONTAINING α-HALO ACETANILIDES AND SUBSTITUTED BICYCLO(3.3.1)NON-2-ENE COMPOUNDS AS SAFENING AGENTS

[75] Inventor: James A. Kloek, Creve Coeur, Mo.

[73] Assignee: Monsanto Company, St. Louis, Mo.

[21] Appl. No.: 80,750

[22] Filed: Oct. 1, 1979

[51] Int. Cl.³ .......................................... A01N 25/32
[52] U.S. Cl. ...................................... 71/106; 71/113; 71/118; 71/119; 71/123
[58] Field of Search ................ 71/106, 113, 118, 119, 71/123

[56] References Cited
U.S. PATENT DOCUMENTS 3,524,884  8/1970  Kretschmar .......................... 260/586
3,547,620  12/1970  Olin ........................................ 71/118

OTHER PUBLICATIONS

Corey et al., J.A.C.S., 87:24 (1965) p. 5728.
Cope et al., J.A.C.S., vol. 72 (1950) p. 5228.
Cope et al., J.A.C.S., vol. 72 (1950) p. 3399.

*Primary Examiner*—Catherine L. Mills
*Attorney, Agent, or Firm*—Gordon F. Sieckmann; Donald W. Peterson

[57] ABSTRACT

The invention relates to the safening of crop plants to the use of herbicides utilizing a substituted bicyclo[3.3.1]non-2-ene or composition containing such compounds to reduce the herbicidal injury to treated crop plants. The invention is also concerned with novel compositions which comprise an alpha-haloacetanilide herbicide and a substituted-bicyclo[3.3.1]non-2-ene.

6 Claims, No Drawings

HERBICIDAL COMPOSITIONS CONTAINING α-HALO ACETANILIDES AND SUBSTITUTED BICYCLO(3.3.1)NON-2-ENE COMPOUNDS AS SAFENING AGENTS

This invention relates to the safening of crop plants to the use of herbicides utilizing a safening agent or composition containing a safening agent to reduce the herbicidal injury to treated crop plants. More specifically, the invention is concerned with the methods of treating the plant crop locus with a substituted bicyclo[3.3.1]-non-2-ene or compositions containing such compounds in order to prevent or reduce the injury to the crop plant which would otherwise occur due to the use of an alpha-haloacetanilide herbicide alone. This invention is also concerned with novel compositions which comprise an acetanilide herbicide and a substituted-bicyclo[3.3.1]non-2-ene.

In practice it has been found that acetanilide herbicides are effective in controlling certain weeds in the presence of growing crops. It has been found that when acetanilide herbicides are applied at rates necessary to stunt or kill the weeds, many of these herbicides injure certain crop plants thus slowing growth and development. This injury results in decreased crop yields, thereby reducing the effectiveness of certain herbicides in controlling weeds in the presence of crops. Obviously, a safening agent or composition thereof, that could be used to treat the crop plant locus, resulting in a reduction of injury due to application of the herbicide without a corresponding reduction of herbicidal action on the weed, would be quite beneficial.

In accordance with the novel aspects of the present invention, crop plants can be protected or the tolerance of said crop plants can be increased to minimize injury due to the application thereto of an acetanilide herbicide, without a corresponding reduction in injury to the weeds by treating the crop plant locus with an effective amount of a safening agent comprising a substituted-bicyclo[3.3.1]non-2-ene having the formula

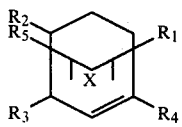

(I)

wherein $R_1$ and $R_2$ are independently hydrogen or lower alkyl; $R_3$ is hydrogen or phenyl; $R_4$ is lower alkyl or selected from the group represented by $R_3$; $R_5$ is hydrogen or a

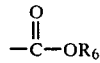

group wherein $R_6$ is selected from the group consisting of hydrogen, lower alkyl and substituted phenyl containing from one to three substituents selected from the group consisting of halogen and trifluoromethyl; and X is oxygen or a

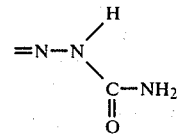

group.

It is preferred that the substituted phenyl radicals represented by $R_6$ contain one or two substituents.

The class of acetanilide herbicides employed in the compositions and methods of this invention include 2-chloro-2',6'-diethyl-N-(methoxymethyl)acetanilide, 2-chloro-2',6'-diethyl-N-(butoxymethyl)acetanilide, 2-chloro-N-(2-methoxy-1-methylethyl)-6'-ethyl-o-acetotoluidide and the like. The preparation and use of 2-chloro-2',6'-diethyl-N-(methoxymethyl)acetanilide and 2-chloro-2',6'-diethyl-N-(butoxymethyl)acetanilide to control the growth of undesired plants is described in U.S. Pat. No. 3,442,945. Herbicidal compositions containing these compounds are disclosed in U.S. Pat. No. 3,547,620. U.S. Pat. No. 3,937,730 discloses 2-chloro-N-(2-methoxy-1-methylethyl)-6'-ethyl-o-acetotoluidide.

Although it has been taught that a wide variety of acetanilides are useful as selective herbicides, it is evident from the prior art that alpha-halocetanilides are most commercially significant. Because of the wide usage of alpha-haloacetanilides, these herbicides are the preferred herbicides for safening by the methods and compositions of the present invention. Nevertheless, the present safening methods and compositions are useful for safening the herbicidal acetanilide family of compounds and the instant invention is not limited to only alpha-haloacetanilide herbicides.

Treatment of the crop plant locus refers to the application of the herbicide and safening agent, in admixture or in sequence, to the plant growth medium as well as directly to the plants or to parts thereof such as roots, stems, leaves, flowers, fruits or other plant parts. Also included in the term is treatment of plant seeds prior to planting with a safening agent.

As employed herein, the term "lower alkyl" designates alkyl radicals which have up to four carbon atoms in a straight or branched chain, such as, for example, methyl, ethyl, propyl, isopropyl, butyl, isobutyl, sec-butyl and t-butyl.

The term "halogen" as used herein includes chloro, bromo, fluoro and iodo.

Illustrative of the substituted phenyl groups which $R_6$ represents are mono-substituted phenyl wherein the substituent is in the ortho, meta or para position, for example, fluorophenyl, chlorophenyl, bromophenyl, iodophenyl and trifluoromethylphenyl, and the di- and tri-substituted phenyl groups wherein the substituents are the same or different and are located in the 2,3,4,5 or 6 positions of the phenyl ring, for example, dichlorophenyl, difluorophenyl, (bromo)(chloro)phenyl,di(trifluoromethylphenyl), chloro(trifluoromethyl)phenyl, trifluorophenyl, trichlorophenyl, tribromophenyl and the like.

The safening agents of this invention may be applied in a mixture with the above-named herbicides, or the components of the mixture can be used sequentially. In the case of a sequential treatment, the safening agent may be applied either before or after application of the herbicide. Effective herbicidal amounts of the particular herbicide employed are well understood by those skilled in the art, and such amounts are used together with an effective safening amount of a substituted-bicyclo-[3.3.1]non-2-ene. The term "effective safening amount" refers to the amount of safening agent required to effectively reduce the crop injury caused by application of a herbicide at a given rate. The amount of safening agent employed in the method and compositions of this invention will vary depending upon the particular herbicide with which the safening agent is employed, the rate of application of the herbicide, the crop to be protected as well as the manner of application of the safening agent. The ratio of herbicide to safening agent may vary depending upon the age of the plants at time of treatment, climatic conditions, soil, etc. It is generally preferred to employ a weight ratio of herbicide to safening agent ranging from about 1:4 to 8:1.

In each test a crop plant, with or without weeds, is grown in a container, and there is an application of the herbicide and a safening agent. In each test there is also a container which receives no application at all, a container to which only the herbicide is applied, and a container to which only the safening agent is applied. The untreated container shows normal plant growth as standard, and it also serves as an indicator of extraneous conditions which may affect the plants. The other containers show the effect of the herbicide alone, the effect of the safening agent alone, and the effect of the application of both. These effects are in terms of percent inhibition of plant growth relative to the plants in the untreated container.

The "safening effect" is determined by adding the percent inhibition obtained when the herbicide is applied alone to the percent inhibition obtained when the safening agent is applied alone (in no instance, however, will thus sum be taken as greater than 100), then subtracting from that sum the percent inhibition obtained when the herbicide and safening agent are both applied. The percent inhibition as used hereinafter refers to the percent injury of weeds or crop plants. Complete inhibition or kill equals 100%.

The effectiveness of the substituted-bicyclo-[3.3.1]-non-2-enes of formula (I) for the purposes of this invention is demonstrated by the results obtained using the various test procedures hereinafter described. Specific individual compounds employed as safening agents in these procedures are identified by the compound number given in Table IV. The herbicides as used in the test procedures was in the form of a formulation comprising the named active ingredient, a solvent and an emulsifier. All rate of application of the herbicide and safening agent in the following examples are shown in kilograms per hectare unless otherwise noted. An asterisk indicates a safening effect of 0 to 19%. In those tests where the procedures are replicated, the results represent an average of all replicates. The compounds as employed in the following examples serve only to illustrate the novel aspects of the invention and should not be construed as a limitation on its scope.

EXAMPLE 1

A good grade of top soil was placed in a container and compacted to a depth of approximately 1.27 cm. from the top of said container. A predetermined number of seeds of each of the crop species to be tested were placed on top of the soil. A quantity of soil sufficient to substantially fill the container was measured and placed in a second container. A measured quantity of the safening agent dispersed or dissolved in a suitable carrier was applied to the soil in the second container. A measured quantity of formulated 2-chloro-2',6'-diethyl-N-(butoxymethyl) acetanilide dispersed or dissolved in a suitable carrier was then sprayed on the soil previously treated with the safening agent. The soil containing the safening agent and herbicide was thoroughly mixed. This mixing is sometimes referred to as incorporation of the herbicide and safening agent into the soil. The mixing or incorporation provides a substantially uniform distribution of the safening agent and herbicide throughout the soil. The seeds were covered with the soil containing the safening agent and herbicide and the pots were leveled. The pots were then placed on a sand bench in the greenhouse and watered from below as needed. The plants were observed at the end of approximately 21 days and the results in terms of percent inhibition of each seed lot were recorded.

The test results in Table I illustrate the reduction in the inhibition of crop plants which was achieved when 2-chloro-2',6'-diethyl-N-(butoxymethyl)acetanilide was used in conjunction with a safening agent of this invention.

TABLE I

| Safening Agent | Safening Agent Rate | Herbicide Rate | Safening Effect | | |
|---|---|---|---|---|---|
| | | | Rice | Sorghum | Wheat |
| 1 | 8.96 | 4.48 | 42 | 20 | 30 |
| 2 | 8.96 | 4.48 | 55 | 60 | 70 |
| 3 | 8.96 | 6.72 | * | 21 | * |
| 4 | 8.96 | 6.72 | 28 | * | 20 |
| 5 | 8.96 | 6.72 | 20 | * | * |
| 6 | 8.96 | 6.72 | * | * | * |
| 7 | 8.96 | 4.48 | 60 | * | * |
| 8 | 8.96 | 6.72 | * | * | * |
| 9 | 8.96 | 6.72 | * | * | * |

EXAMPLE 2

A good grade of top soil was placed in a plastic pot. A measured quantity of the safening agent dispersed or dissolved in a suitable carrier was sprayed on the soil surface. A measured quantity of formulated 2-chloro-2',6'-diethyl-N-(butoxymethyl)acetanilide dispersed or dissolved in a suitable carrier was sprayed on the soil surface. Pre-soaked rice was seeded into the pots that were previously flooded with water. The water level was lowered to the soil surface after 24 hours and maintained at this level for 5 days after which the pots were reflooded for the duration of the test. The plants were observed at the end of approximately 21 days and the results in terms of the precent inhibition of rice are recorded.

The test results in Table II further illustrate the reduction in the inhibition of rice plants which was achieved when 2-chloro-2',6'-diethyl-N-(butoxymethyl) acetanilide was used in conjunction with a safening agent of this invention. Individual data was not included at application rates at which the herbicide did not produce any crop injury.

TABLE II

| Safening Agent | Safening Agent Rate | Herbicide Rate | Safening Effect |
|---|---|---|---|
| 1 | 0.56 | 0.07 | * |
| | 0.56 | 0.28 | * |
| | 0.56 | 1.12 | * |
| 2 | 0.56 | 0.07 | * |
| | 0.56 | 0.28 | 28 |
| | 0.56 | 1.12 | * |

TABLE II-continued

| Safening Agent | Safening Agent Rate | Herbicide Rate | Safening Effect |
| --- | --- | --- | --- |
| 7 | 0.56 | 0.07 | 31 |
|  | 0.56 | 0.28 | * |
|  | 0.56 | 1.12 | * |

EXAMPLE 3

The procedure of Example 1 was employed utilizing 2-chloro-2',6'-diethyl-N-(methoxymethyl)acetanilide as the herbicide.

The test results in Table III illustrate the reduction in the inhibition of crop plants which was achieved when 2-chloro-2',6'-diethyl-N-(methoxymethyl)acetanilide was used in conjunction with a safening agent of this invention.

TABLE III

| Safening Agent | Safening Agent Rate | Herbicide Rate | Safening Effect |||
| --- | --- | --- | --- | --- | --- |
| | | | Rice | Sorghum | Wheat |
| 1 | 8.96 | 2.24 | 54 | * | * |
| 2 | 8.96 | 2.24 | * | * | * |
| 3 | 8.96 | 4.48 | * | * | * |
| 4 | 8.96 | 4.48 | * | * | * |
| 5 | 8.96 | 4.48 | * | * | 25 |
| 6 | 8.96 | 4.48 | * | * | 20 |
| 7 | 8.96 | 2.24 | 20 | * | * |
| 8 | 8.96 | 4.48 | * | 20 | * |
| 9 | 8.96 | 4.48 | * | 75 | * |

Most of the preceding examples show the use of the described test procedures with more than one safening agent of this invention. It should be understood that all of the tests within a single example were not necessarily conducted at the same time. It should also be understood, that an untreated container, plus containers with the herbicide alone and the safening agent alone, are employed for each test initiation date as controls to obtain the herbicide and safening effect data for tests begun on that particular date.

The above examples illustrate that while the substituted-bicyclo[3.3.1]non-2-enes of the present invention generally safen crop plants, especially rice, sorghum and wheat crops to the herbicidal effects of acetanilide herbicides, those skilled in the art will appreciate that the compounds of the invention may be used most effectively in safening rice against injury due to the herbicidal effects of 2-chloro-2',6'-diethyl-N-(butoxymethyl)acetanilide.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal, higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylammonium compounds, sodium salts of petroleum-derived alkylsulfonic acids, polyethylene sorbitan monooleate, alkylaryl polyether alcohols, water-soluble lignin sulfonate salts, alkalicasein compositions, long chain alcohols usually containing 10–18 carbon atoms, and condensation products of ethylene oxide with fatty acids, alkylphenols and mercaptans.

U.S. Pat. No. 3,524,884 describes the intramolecular cyclization of cis-4-cyclooctene-1-carboxylic acid to form bicyclo[3.3.1]-non-2-en-9-one which is used in perfumes and flavor compositions.

The compounds of formula (I) which are employed in the method of the present invention may be prepared utilizing procedures such as described by Corey and Nozoe in *JACS*, 87:24, Dec. 20, 1965, p. 5728; by Cope and Synerholm in *JACS* Vol. 72, Nov. 1950, p. 5228 and by Cope et al. in *JACS* Vol. 72, Aug. 1950, p 3399.

In accordance with known procedures the following compounds found in Table IV have been prepared.

TABLE IV

| Safening Agent | Compound | Physical Constants b.p. °C. | m.p. °C. |
| --- | --- | --- | --- |
| (1) | 1,2-dimethyl-6-isopropyl-bicyclo[3.3.1]non-2-en-9-one | 79-81 @0.2 mmHg | — |
| (2) | 2,4-diphenyl-bicyclo[3.3.1]non-2-en-9-one | — | 139-143 |
| (3) | 9-oxo-bicyclo[3.3.1]non-3-ene-1-carboxylic acid | — | 133-135 |
| (4) | ethyl ester of 9-oxo-bicyclo[3.3.1]non-3-ene-1-carboxylic acid | 60 @0.1 mmHg | — |
| (5) | 2,4-dichlorophenyl ester of 9-oxo-bicyclo[3.3.1]non-3-ene-1-carboxylic acid | 150 @0.1 mmHg | — |
| (6) | 3-(trifluoromethyl)phenyl ester of 9-oxo-bicyclo[3.3.1]non-3-ene-1-carboxylic acid | 150 @0.1 mmHg | — |
| (7) | 1,2-dimethyl-6-isopropyl-bicyclo[3.3.1]non-2-en-9-semicarbazone | — | 159-170 |
| (8) | ethyl ester of 9-[(aminocarboxyl)hydrazono]-bicyclo[3.3.1]non-3-ene-1-carboxylic acid | — | 199-200 |
| (9) | 2,4-diphenyl-bicyclo[3.3.1]non-2-en-9-semicarbazone | — | 143-150 |

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A composition comprising a herbicidally effective amount of 2-chloro-2',6'-diethyl-N-(methoxymethyl) acetanilide and an effective safening amount of a compound selected from the group consisting of 2,4-dichlorophenyl ester of 9-oxo-bicyclo[3.3.1]non-3-ene-1-carboxylic acid, 3-(trifluoromethyl)phenyl ester of 9-oxo-bicyclo[3.3.1]non-3-ene-1-carboxylic acid and 2,4-diphenyl-bicyclo[3.3.1]non-2-en-9-semicarbazone.

2. A composition according to claim 1, wherein said compound is 2,4-dichlorophenyl ester of 9-oxo-bicyclo[3.3.1]non-3-ene-1-carboxylic acid.

3. A composition according to claim 1 wherein said compound is 3-(trifluoromethyl)phenyl ester of 9-oxo-bicyclo[3.3.1]non-3-ene-1-carboxylic acid.

4. A composition according to claim 1 wherein said compound is 2,4-diphenyl-bicyclo[3.3.1]non-2-en-9-semicarbazone.

5. A method for reducing herbicidal injury to wheat crop plants which comprises treating the plant locus with a herbicidally effective amount of 2-chloro-2',6'-diethyl-N-(methoxymethyl) acetanilide and an effective safening amount of 2,4-dichlorophenyl ester of 9-oxo-bicyclo[3.3.1]non-3-ene-1-carboxylic acid or 3-(trifluoromethyl)phenyl ester of 9-oxo-bicyclo[3.3.1]non-3-ene-1-carboxylic acid.

6. A method for reducing herbicidal injury to sorghum crop plants which comprises treating the plant locus with a herbicidally effective amount of 2-chloro-2',6'-diethyl-N-methoxymethyl) acetanilide and an effective safening amount of 2,4-diphenyl-bicyclo[3.3.1]-non-2-en-9-semicarbazone.

* * * * *